United States Patent
Furukawara et al.

(10) Patent No.: US 9,326,923 B2
(45) Date of Patent: May 3, 2016

(54) WATER-IN-OIL-TYPE SKIN-WHITENING COSMETIC

(75) Inventors: Tomomi Furukawara, Yokohama (JP); Takayuki Omura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/233,946

(22) PCT Filed: Jul. 13, 2012

(86) PCT No.: PCT/JP2012/067888
§ 371 (c)(1),
(2), (4) Date: Feb. 27, 2014

(87) PCT Pub. No.: WO2013/024653
PCT Pub. Date: Feb. 21, 2013

(65) Prior Publication Data
US 2014/0186281 A1    Jul. 3, 2014

(30) Foreign Application Priority Data

Aug. 12, 2011 (JP) .................. 2011-176507

(51) Int. Cl.
| | | |
|---|---|---|
| *A61K 8/36* | (2006.01) | |
| *A61K 8/25* | (2006.01) | |
| *A61Q 19/02* | (2006.01) | |
| *A61K 8/368* | (2006.01) | |
| *A61K 8/02* | (2006.01) | |
| *A61K 8/06* | (2006.01) | |

(52) U.S. Cl.
CPC ............... *A61K 8/361* (2013.01); *A61K 8/0254* (2013.01); *A61K 8/064* (2013.01); *A61K 8/25* (2013.01); *A61K 8/368* (2013.01); *A61Q 19/02* (2013.01); *A61K 2800/612* (2013.01); *A61K 2800/651* (2013.01)

(58) Field of Classification Search
CPC ..... A61K 8/361; A61K 8/0254; A61K 8/368; A61K 8/064; A61K 8/25; A61K 2800/612; A61K 2800/651; A61Q 19/02
See application file for complete search history.

(56) References Cited

U.S. PATENT DOCUMENTS

2005/0061205 A1*  3/2005  Kobayashi et al. ........... 106/415
2011/0318399 A1* 12/2011  Sasaki et al. .................. 424/401

FOREIGN PATENT DOCUMENTS

| JP | 6-40886 | 2/1994 |
|---|---|---|
| JP | H07173023 | 7/1995 |
| JP | 2005-432807 | 5/2005 |
| JP | 2005132807 | 5/2005 |

OTHER PUBLICATIONS

JP-A 2005-132807 and MT.pdf.*
Human translation-in-part of JP-A 2005-132807A.*
JPO Notice of Reasons for Rejection dated Oct. 5, 2012, 3 pages—English; 3 pages—Japanese.
JPO Decision to Grant dated Dec. 14, 2012, 3 pages—English; 3 pages—Japanese.
Applicant's Submitted Written Arguments and Amendments dated Nov. 20, 2012, 5 pages—English; 4 pages—Japanese.
Granted Claims, 1 page—English; 9 pages—Japanese.
PCT/JP2012/067888 International Search Report, mailed Oct. 9, 2012, 1 page—English; 2 pages—Japanese.

* cited by examiner

*Primary Examiner* — Robert A Wax
*Assistant Examiner* — Thor Nielsen
(74) *Attorney, Agent, or Firm* — Andrew F. Young, Esq.; Lackenbach Siegel, LLP

(57) ABSTRACT

Disclosed is a water-in-oil-type skin-whitening cosmetic, which has a moist feel without stickiness when used and has good emulsion stability over time even when accommodated in a glass container or a metal container. The water-in-oil-type skin-whitening cosmetic is characterized in that it contains an alkoxysalicylic acid or a salt thereof, an organic modified clay mineral, and a liquid fatty acid. It is preferable that the liquid fatty acid is selected from higher fatty acids having 12 to 22 carbon atoms and having a linear or branched alkyl chain, such as oleic acid, linolic acid, linolenic acid, and isostearic acid.

4 Claims, No Drawings

WATER-IN-OIL-TYPE SKIN-WHITENING COSMETIC

CROSS REFERENCE TO RELATED APPLICATIONS

This application claims priority to International Ser. No. PCT/JP2012/067888 filed Jul. 13, 2012, the entire contents of which are incorporated herein fully by reference, which in turn claims priority to JP Ser. No. JP 2011-176507 filed on Aug. 12, 2011.

TECHNICAL FIELD

The present invention relates to a water-in-oil-type skin-whitening cosmetic, which has a system in which potassium 4-methoxysalicylate, known as a whitening agent, is added to an emulsion base containing an organic modified clay mineral, and has a moist feel without stickiness when used and good emulsion stability over time regardless of the container material.

BACKGROUND ART

It is conceived that the pigmentation such as speckles and freckles on the skin is caused when melanin is generated excessively due to hormonal disorders, the ultraviolet ray, or skin local inflammation and it deposits in the skin. The melanin, which causes skin pigmentation, is produced in melanocytes present in the epidermal basal layer. The melanin is produced when tyrosine is converted to dopaquinone by the action of an enzyme tyrosinase, subsequently further oxidized, polymerized, and changed to dark melanin.

Conventionally, it has been demanded to alleviate such skin pigmentation and realize a transparent white skin, which is so-called whitening of the skin. Alkoxysalicylic acid or a salt thereof is known as an active ingredient having good whitening effect for alleviating and preventing the abnormal deposit of melanin in the skin. However, generally, when alkoxysalicylic acid or a salt thereof is added to a water-in-oil-type emulsion composition, the stability over time is poor, sometimes posing a problem of causing phase separation between the oil phase and aqueous phase.

To improve the stability over time, a method in which the amount of a lipophilic emulsifier is increased, a method in which a wax is added to an external phase (oil phase), or the like, is used; however, these methods sometimes deteriorate a feel of use with respect to the spreadness and stickiness of a cosmetic. Thus, to improve these problems of the stability and the feel of use, it has been proposed that salts as a buffer and polyethylene glycol having a weight average molecular weight of 1,000 to 200,000 are added in predetermined amounts to a water-in-oil-type skin external emulsion containing alkoxysalicylic acid or a salt thereof (Patent Document 1).

On the other hand, an organic modified clay mineral such as Bentone is commonly added to a water-in-oil-type emulsion composition, not only to a water-in-oil-type emulsion composition containing alkoxysalicylic acid or a salt thereof, as a viscosity adjustor or emulsion stabilizer and also for the purpose of imparting a moist feel when used. Actually, the above Patent Document 1 also discloses production examples containing alkoxysalicylic acid or a salt thereof and an organic modified clay mineral (Examples 8 to 10).

CITATION LIST

Patent Document

Patent Document 1: Japanese Patent No. 4073389

SUMMARY OF INVENTION

Problem to be Solved by the Invention

When both alkoxysalicylic acid or a salt thereof and an organic modified clay mineral are added to a water-in-oil-type emulsion composition, however, the emulsion stability of the composition when filled in a container composed of a hydrophilic material such as glass or metal is deteriorated on the surface between the container and the composition, at which water is leached causing a gap (a peel from the wall) between the container wall surface and the content, whereby such problems as content slips from the container wall surface may occur. As a result, the container for accommodating the composition is limited to those composed of a hydrophobic material such as a resin, thereby reducing the selection option of the product form which was not much satisfactory neither for the user or the manufacturer.

Under these circumstances, an object of the present invention is to provide a water-in-oil-type skin-whitening cosmetic, which has a moist feel without stickiness when used and has good emulsion stability over time even when accommodated in a glass container or a metal container.

Solution to Problem

The present inventors carried out extensive studies to solve the above problems and found that a water-in-oil-type skin-whitening cosmetic having a smooth feel without stickiness when used and having good emulsion stability over time even when accommodated in a container composed of any material such as glass, metal, resin, or ceramic can be obtained when a liquid fatty acid is added to a water-in-oil-type emulsion composition containing alkoxysalicylic acid or a salt thereof and an organic modified clay mineral, whereby the present invention was accomplished.

More specifically, the present invention is summarized as follows.
(1) A water-in-oil-type skin-whitening cosmetic containing an alkoxysalicylic acid or a salt thereof, an organic modified clay mineral, and a liquid fatty acid.
(2) The water-in-oil-type skin-whitening cosmetic according to (1), wherein the alkoxysalicylic acid is represented by the following general formula (I):

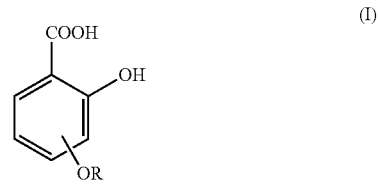

wherein R represents a lower alkyl group having 1 to 6 carbon atoms.
(3) The water-in-oil-type skin-whitening cosmetic according to (2), wherein the alkoxysalicylic acid or a salt thereof is potassium 4-methoxysalicylate.

(4) The water-in-oil-type skin-whitening cosmetic according to any one of (1) to (3), wherein the organic modified clay mineral is dimethyl distearyl ammonium hectorite.
(5) The water-in-oil-type skin-whitening cosmetic according to any one of (1) to (4), wherein the liquid fatty acid is selected from higher fatty acids having 12 to 22 carbon atoms and having a linear or branched, saturated or unsaturated hydrocarbon group.
(6) The water-in-oil-type skin-whitening cosmetic according to any one of (1) to (5), wherein the alkoxysalicylic acid or a salt thereof is 0.001 to 20.0% by mass based on the total amount of the water-in-oil-type skin-whitening cosmetic.
(7) The water-in-oil-type skin-whitening cosmetic according to any one of (1) to (6), wherein the organic modified clay mineral is 0.1 to 5.0% by mass based on the total amount of the water-in-oil-type skin-whitening cosmetic.
(8) The water-in-oil-type skin-whitening cosmetic according to any one of (1) to (7), wherein the liquid fatty acid is 0.01 to 5.0% by mass based on the total amount of the water-in-oil-type skin-whitening cosmetic.
(9) A whitening cosmetic product comprising the water-in-oil-type skin-whitening cosmetic according to any one of (1) to (8) accommodated in a container.

Advantageous Effects of Invention

The water-in-oil-type skin-whitening cosmetic of the present invention has far better emulsion stability by adding a liquid fatty acid to a water-in-oil-type emulsion composition containing an alkoxysalicylic acid or a salt thereof and an organic modified clay mineral than the case in which a liquid fatty acid is not added, and thus can suppress the occurrence of peels and slips from the wall at the container wall surface regardless of the container material. Further, the cosmetic contains an organic modified clay mineral, which conversely obviates the need of adding a large amount of a lipophilic emulsifier or wax, thereby providing a moist feel without stickiness when used.

DESCRIPTION OF EMBODIMENTS

The water-in-oil-type skin-whitening cosmetic of the present invention contains an alkoxysalicylic acid or a salt thereof, an organic modified clay mineral, and a liquid fatty acid. The present invention is described below in detail.

Although the alkoxysalicylic acid or a salt thereof is not particularly limited as long as it can be used in the fields of cosmetic products, pharmaceutical products, and quasi drugs, in the present invention an alkoxysalicylic acid represented by the following general formula (I), that is, a salicylic acid compound in which any of the hydrogen atom at position 3, 4 or 5 of salicylic acid is replaced with an alkoxy group (—OR), or a salt thereof is used.

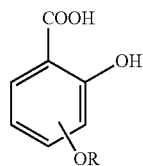
(I)

In the above general formula (I), the alkyl group (R) constituting the alkoxy group (—OR) is a lower alkyl group having 1 to 6 carbon atoms. Both linear and branched alkyl groups are encompassed. Specifically, examples include a methyl group (corresponding alkoxy group —OR: methoxy group), an ethyl group (the same as above: ethoxy group), a propyl group (the same as above: propoxy group), an isopropyl group (the same as above: isopropoxy group), a butyl group (the same as above: butoxy group), and an isobutyl group (the same as above: isobutoxy group), but are not limited thereto.

Specific examples of the alkoxysalicylic acid represented by the above general formula (I) include 3-methoxysalicylic acid (2-hydroxy-3-methoxybenzoic acid), 3-ethoxysalicylic acid (2-hydroxy-3-ethoxybenzoic acid), 4-methoxysalicylic acid (2-hydroxy-4-methoxybenzoic acid), 4-ethoxysalicylic acid (2-hydroxy-4-ethoxybenzoic acid), 4-propoxysalicylic acid (2-hydroxy-4-propoxybenzoic acid), 4-isopropoxysalicylic acid (2-hydroxy-4-isopropoxybenzoic acid), 4-butoxysalicylic acid (2-hydroxy-4-buthoxybenzoic acid), 5-methoxysalicylic acid (2-hydroxy-5-methoxybenzoic acid), 5-ethoxysalicylic acid (2-hydroxy-5-ethoxybenzoic acid), and 5-propoxysalicylic acid (2-hydroxy-5-propoxybenzoic acid).

The alkoxysalicylic acid is an already known substance, and, for example, 5-methoxysalicylic acid and 4-methoxysalicylic acid can be easily synthesized by the method described in "Beil 10227" and "Beil 10379", respectively. Also, it is commercially available as a reagent from Aldrich (Germany), or the like, which can also be used.

A salt of the alkoxysalicylic acid is also encompassed, and the kind of such a salt is not particularly limited as long as the salt is pharmaceutically acceptable, and examples of the salt include alkali metal salts such as sodium salt and potassium salt, alkaline earth metal salts such as calcium salt, ammonium salts, and amino acid salts.

Particularly, potassium 4-methoxysalicylate can be preferably used in light of the whitening effects and easy availability.

One or more alkoxysalicylic acid or a salt thereof can be added. The incorporation amount of alkoxysalicylic acid or a salt thereof is not particularly limited, but typically 0.001 to 20.0% by mass, preferably 0.01 to 10.0% by mass, further preferably 0.5 to 3.0% by mass, based on the total amount of the water-in-oil-type skin-whitening cosmetic. When the amount is below 0.001% by mass, a sufficient whitening effect is difficult to be exhibited, whereas when the amount exceeding 20.0% by mass is added, the whitening effect improvement according to the increased amount is not easily achieved and rather a sticky feel tends to appear, which are hence not preferable.

The organic modified clay mineral is preferably those in which a quaternary ammonium salt compound is added to a natural or synthetic smectite clay mineral such as bentonite by the ion exchange reaction. The organic modified clay mineral is not particularly limited as long as it is pharmaceutically acceptable, and examples include dimethyl ammonium hectorite, benzyl dimethyl stearyl ammonium hectorite, and magnesium aluminum silicate treated with distearyl dimethyl ammonium chloride. Preferable examples of the commercial product include dimethyl distearyl ammonium hectorite sold under the name of "Bentone 38VCG" from Elementis Plc and benzyl dimethyl stearyl ammonium hectorite sold under the name of "Bentone 27VCG" from Elementis Plc.

One or more organic modified clay mineral can be added. The incorporation amount of the organic modified clay mineral is not particularly limited and typically 0.1 to 5.0% by mass based on the total amount of the water-in-oil-type skin-whitening cosmetic. When the amount is below 0.1% by mass, the emulsion stability is likely to decrease, whereas when the amount exceeding 5.0% by mass is added, stickiness and a poor feel of use tend to appear, which are hence not preferable.

The liquid fatty acid that can be used is a higher fatty acid having 12 to 22 carbon atoms and having a linear or branched, saturated or unsaturated hydrocarbon group and in the liquid form at ordinary temperature (25° C.). Examples of the liquid fatty acid include linear chain fatty acids such as oleic acid, linolic acid, and linolenic acid, and branched chain fatty acids such as isopalmitic acid and isostearic acid. These liquid fatty acids can be easily mixed when the water-in-oil-type skin-whitening cosmetic is produced, and have good compatibility with other addition ingredients.

One or more liquid fatty acid can be added. The incorporation amount of the liquid fatty acid is 0.01 to 5.0% by mass based on the total amount of the water-in-oil-type skin-whitening cosmetic. When the amount is below 0.01% by mass, the sufficient stabilization cannot be achieved and slips and peels from the wall when the cosmetic is accommodated in a glass or metal container are likely to be caused. On the other hand, when the amount exceeding 5.0% by mass is added, the stability improvement according to the increased amount is not easily achieved.

The water-in-oil-type skin-whitening cosmetic of the present invention is in the form of a water-in-oil-type emulsion composition containing an aqueous phase (internal phase) and an oil phase (external phase). Since the form of a water-in-oil-type emulsion composition is required, a low HLB emulsifier, preferably an emulsifier having an HLB of 7 or less, is used. Examples of the emulsifier having an HLB of 7 or less include sorbitan fatty acid esters such as sorbitan monolaurate, sorbitan monooleate, sorbitan monoisostearate, and sorbitan tristearate; glycerol fatty acid esters such as glycerol monostearate, glycerol monooleate, glycerol isostearate, diglycerol diisostearate, and polyglyceryl-10 pentaisostearate; polyoxyethylene hydrogenated castor oils such as POE (5), POE (7.5), and POE (10) hydrogenated castor oils; high molecular weight lipophilic surfactants such as dipolyhydroxystearates: polyglyceryl-2 dipolyhydroxystearate (product of Cognis Holding GmbH: PGPH) and PEG30 dipolyhydroxystearate (product of Uniqema: Arlacel P-135); polyether silicones such as cetyl dimethicone copolyols [e.g., "ABIL EM90" (product of Goldschmidt)], polyether modified silicone [e.g., "SC 9450" (product of Shin-Etsu Chemical Co., Ltd.)], and crosslinked polyether modified silicone [e.g., "KSG" series (product of Shin-Etsu Chemical Co., Ltd.)]; and polyglycerol silicones such as polyglycerol modified silicone and alkyl co-modified polyglycerol modified silicone. In the present invention, one or more emulsifier having an HLB of 7 or less can be used. Particularly, polyether silicone emulsifiers or polyglycerol silicone emulsifiers are preferably used.

The emulsifier having an HLB of 7 or less is added in an amount of preferably 0.01 to 10.0% by mass, more preferably 0.1 to 5.0% by mass, based on the total amount of the water-in-oil-type skin-whitening cosmetic. When the incorporation amount of the emulsifier is below 0.01% by mass, the emulsion is likely to be unstable because the emulsion particles are unified as time passes, whereas when the amount exceeding 10.0% by mass is added, a heavy sticky feel is likely to be caused when used.

In addition to the above addition ingredients, the water-in-oil-type skin-whitening cosmetic of the present invention can contain as necessary other components commonly used in cosmetic products, pharmaceutical products, and the like, such as moisturizers, buffers, dispersants, chelating agents, preservatives, perfumes, surfactants (excluding the above emulsifiers having an HLB of 7 or less), ultraviolet absorbing agents, or drugs, within the range wherein the effects of the present invention are not impaired, but the component is not limited to those given here.

The water-in-oil-type skin-whitening cosmetic of the present invention can be prepared by a routine method, and the emulsification method is not particularly limited. Examples of the method include a method in which an aqueous phase (internal phase) and an oil phase (external phase) prepared individually are each heated to about 80° C., the heated aqueous phase is gradually added to the oil phase and emulsified using an emulsifying apparatus, and subsequently allowed to cool to room temperature.

The container for accommodating the water-in-oil-type skin-whitening cosmetic of the present invention may be those formed of various materials typically used in the field of cosmetic products. For example, metal containers formed of aluminum, stainless steel, or the like, resin containers formed of polyethylene, polypropylene, polyethylene terephthalate, polyamide, polycarbonate, or the like, glass containers, and ceramic containers can be used. The water-in-oil-type skin-whitening cosmetic of the present invention can be provided in the form of a whitening cosmetic product accommodated in these containers.

EXAMPLES

Hereinafter, the present invention is described in further detail with reference to Examples, but is not limited to these Examples. Additionally, the incorporation amount, unless otherwise stated, is shown by % by mass based on the total amount of water-in-oil-type skin-whitening cosmetic.

The evaluation method employed in each Example is described before Examples are illustrated.

[Usability Evaluation (Stickilessness)]

10 panelists were asked to use the water-in-oil-type skin-whitening cosmetics (samples) of each Example and Comparative Example and evaluate for the absence of stickiness on skin in accordance with the following evaluation criteria.

(Evaluation)

○: 8 or more panelists sensed no stickiness on the skin

Δ: 4 to 7 panelists sensed no stickiness on the skin

X: 3 or less panelists sensed no stickiness on the skin

[Stability Evaluation]

Each sample obtained in Examples and Comparative Examples was put in each of a resin container composed mainly of polyethylene terephthalate and a glass container, allowed to stand at 40° C. for 1 month, examined with the naked eyes for the occurrence of peels and slips from the wall between the container and content, and evaluated in accordance with the following evaluation criteria.

(Evaluation)

○: No peel or slip from the wall was found between the container and content.

X: A peel or slip from the wall was found between the container and content.

Examples 1 to 3 and Comparative Examples 1 to 3

The water-in-oil-type emulsion compositions having the composition shown in Table 1 below were prepared to use as the samples and evaluated for the usability and stability in accordance with the above evaluation criteria. Table 1 collectively shows the results.

(Production Method)

The oil soluble ingredients ((6) to (8) and (23) to (25)) were dissolved in the oil ingredients ((9) to (16)) and heated to 80° C. to prepare an oil phase. On the other hand, the water soluble ingredients ((2) to (5) and (17) to (22)) were dissolved in the purified water (1) and heated to 80° C. to prepare an aqueous phase. Subsequently, the obtained aqueous phase was stirred and mixed with the oil phase while gradually added, and the mixture was cooled to room temperature, thereby obtaining a cream.

TABLE 1

| Classification | Name of raw materials | Comparative Example 1 (%) | Comparative Example 2 (%) | Comparative Example 3 (%) | Example 1 (%) | Example 2 (%) | Example 3 (%) |
|---|---|---|---|---|---|---|---|
| Water | (1) Purified water | 49.94 | 49.44 | 48.94 | 48.44 | 43.94 | 45.94 |
| Moisturizer | (2) Glycerol | 8 | 8 | 8 | 8 | 8 | 8 |
|  | (3) Butylene glycol | 7 | 7 | 7 | 7 | 7 | 7 |
|  | (4) Sorbitol | 2 | 2 | 2 | 2 | 2 | 2 |
|  | (5) PEG-150 | 1 | 1 | 1 | 1 | 1 | 1 |
| Surfactant | (6) PEG-9 polydimelhylsiloxyethyl dimethicone | 1.7 | 1.7 | 1.7 | 1.7 | 1.7 | 1.7 |
|  | (7) PEG-8 diisostearate | 0.4 | 0.4 | 0.4 | 0.4 | 0.4 | 0.4 |
| Clay mineral | (8) Dimethyl distearyl ammonium hectorile | 2.1 | 2.1 | 2.1 | 2.1 | 2.1 | 2.1 |
| Oil ingredient | (9) Cetyl ethylhexanoate | 6 | 6 | 6 | 6 | 6 | 6 |
|  | (10) Olefin oligomer | 12 | 12 | 12 | 12 | 12 | 12 |
|  | (11) Squalane | 1 | 1 | 1 | 1 | 1 | 1 |
|  | (12) Isohexadecane | 4 | 4 | 4 | 4 | 4 | 4 |
|  | (13) Microcrystalline wax | 3 | 3 | 3 | 3 | 3 | 3 |
|  | (14) Vaseline | 1 | 1 | 1 | 1 | 1 | 1 |
|  | (15) Isostearic acid |  |  |  | 0.5 |  | 1 |
|  | (16) Oleic acid |  |  |  |  | 5 |  |
| Drug | (17) Potassium 4-methoxysalicylate |  | 0.5 | 1 | 1 | 1 | 3 |
| Buffer | (18) Citric acid | 0.02 | 0.02 | 0.02 | 0.02 | 0.02 | 0.02 |
|  | (19) Sodium citrate | 0.08 | 0.08 | 0.08 | 0.08 | 0.08 | 0.08 |
| Dispersant | (20) Na metaphosphate | 0.01 | 0.01 | 0.01 | 0.01 | 0.01 | 0.01 |
| Chelating agent | (21) EDTA-3NA,2H2O | 0.1 | 0.1 | 0.1 | 0.1 | 0.1 | 0.1 |
| Preservative | (22) Phenoxyethanol | 0.3 | 0.3 | 0.3 | 0.3 | 0.3 | 0.3 |
|  | (23) Methylparaben | 0.15 | 0.15 | 0.15 | 0.15 | 0.15 | 0.15 |
|  | (24) Ethylparaben | 0.1 | 0.1 | 0.1 | 0.1 | 0.1 | 0.1 |
| Perfume | (25) Perfume | 0.1 | 0.1 | 0.1 | 0.1 | 0.1 | 0.1 |
| Usability | Stickiness | ○ | ○ | ○ | ○ | ○ | ○ |
| Stability | Resin container | ○ | ○ | ○ | ○ | ○ | ○ |
|  | Glass container | ○ | x | x | ○ | ○ | ○ |

As evident from the results shown in Table 1, when potassium 4-methoxysalicylate, a whitening agent, was added to the water-in-oil-type emulsion composition containing an organic modified clay mineral (Comparative Example 1), the stability had no problem in the resin container but when accommodated in the glass container, peels and slips from the wall were found between the container and content (Comparative Examples 2 and 3). On the other hand, when the liquid fatty acid such as isostearic acid or oleic acid was added to the oil phase, no peel or slip from the wall was found in the glass container as well as the resin container even when potassium 4-methoxysalicylate was added, thereby verifying the significant improvement of stability. Further, stickiness was not caused from the addition of the liquid fatty acid, revealing that the usability was also good.

Example 4

Whitening Cream

| Addition ingredients | % by mass |
|---|---|
| (1) Purified water | balance |
| (2) Ethanol | 3 |
| (3) Glycerol | 3 |
| (4) Dipropylene glycol | 5 |
| (5) PEG-150 | 2 |
| (6) PEG-10 dimethicone | 3 |
| (7) Dimethyl distearylammonium hectorite | 1.5 |
| (8) Dimethicone | 20 |
| (9) Olefin oligomer | .5 |
| (10) Tsostearic acid | 0.5 |
| (11) Potassium 4-methoxysalicylate | 1 |
| (12) Tranexamic acid | 1 |
| (13) Citric acid | 0.02 |
| (14) Sodium citrate | 0.08 |
| (15) Disodium edetate | 0.1 |
| (16) Phenoxyethanol | 0.5 |
| (17) Perfume | Proper quantity |

Production Method:

The oil soluble ingredients ((6), (7) and (17)) were dissolved in the oil ingredients ((8) to (10)) and heated to 80° C. (oil phase). On the other hand, the water soluble ingredients ((2) to (5) and (11) to (16)) were dissolved in the purified water (1) and heated to 80° C. (aqueous phase). The obtained aqueous phase was stirred and mixed with the oil phase while gradually added, and the mixture was cooled to room temperature, thereby obtaining a cream.

The cream was evaluated by the same method as above and it was verified that no peel or slip from the wall was found even when the cream was accommodated in a glass container, stickiness was not caused and the usability was also good.

Example 5

Whitening Cream

| Addition ingredients | % by mass |
| --- | --- |
| (1) Purified water | balance |
| (2) Glycerol | 10 |
| (3) Butylene glycol | 5 |
| (4) Dimethyl distearyl ammonium hectorite | 2.5 |
| (5) Cetyl dimethicone copolyol | 2 |
| (6) PEG-10 dimethicone | 1 |
| (7) Decamethyl cyclotetrasiloxane | 20 |
| (8) Squalane | 5 |
| (9) Cetyl 2-ethylhexanoate | 1 |
| (10) Oleic acid | 1 |
| (11) Potassium 4-methoxysalicylate | 1 |
| (12) Dipotassium glycyrrhizinate | 0.05 |
| (13) Sodium hexametaphosphate | 0.03 |
| (14) Phenoxyethanol | 0.5 |
| (15) Perfume | Proper quantity |

Production Method:

The oil soluble ingredients ((4) to (6) and (15)) were dispersed in the oil ingredients ((7) to (10)) (oil phase), whereas the water soluble ingredients ((2), (3) and (11) to (14)) were dissolved in the purified water (1) (aqueous phase). The obtained aqueous phase was stirred and mixed with the oil phase while gradually added, thereby obtaining a cream.

The cream was evaluated by the same method as above and it was verified that no peel or slip from the wall was found even when the cream was accommodated in a glass container, stickiness was not caused and the usability was also good.

The invention claimed is:

1. A whitening cosmetic product comprising a water-in-oil type skin-whitening cosmetic comprising:
   0.001 to 20.0% by mass of potassium 4-methoxysalicylate,
   0.1 to 5.0% by mass of an organic modified clay mineral, and
   0.01 to 5.0% by mass of oleic acid and/or isostearic acid, accommodated in a glass container, wherein the occurrence of peels and slips from the container walls is suppressed, relative to the product formulated without oleic or isostearic acid.

2. The whitening cosmetic product according to claim 1, wherein the organic modified clay mineral is dimethyl distearyl ammonium hectorite.

3. A method for suppressing the occurrence of peels and slips from the container walls in a water-in-oil skin-whitening cosmetic comprising 0.001 to 20.0% by mass of potassium 4-methoxysalicylate and 0.1 to 5.0% by mass of an organic modified clay mineral, when the cosmetic is accommodated in a glass container, comprising the step of incorporating into the cosmetic 0.01 to 5.0% by mass of oleic acid and/or isostearic acid.

4. The method of claim 3, wherein the organic modified clay mineral is dimethyl distearyl ammonium hectorite.

* * * * *